United States Patent [19]

Wagner et al.

[11] 4,143,060
[45] Mar. 6, 1979

[54] PROCESS FOR THE PREPARATION OF SILYL SUBSTITUTED UREA DERIVATIVES

[75] Inventors: Kuno Wagner, Leverkusen; Günter Oertel, Cologne, both of Fed. Rep. of Germany; Hans D. Gölitz, deceased, late of Mettmann, Fed. Rep. of Germany, by Ingrid I. K. Gölitz, heiress; Bernd Quiring, Leverkusen, Fed. Rep. of Germany

[73] Assignee: Bayer Aktiengesellschaft, Leverkusen, Fed. Rep. of Germany

[21] Appl. No.: 535,537

[22] Filed: Dec. 23, 1974

Related U.S. Application Data

[63] Continuation-in-part of Ser. No. 303,183, Nov. 2, 1972, abandoned.

[30] Foreign Application Priority Data

Nov. 6, 1971 [DE] Fed. Rep. of Germany ....... 2155260

[51] Int. Cl.² .......................... C07F 7/02; C07F 7/07
[52] U.S. Cl. ...................... 260/448.2 N; 260/448.2 R
[58] Field of Search ................. 260/448.2 R, 448.2 N

[56] References Cited

U.S. PATENT DOCUMENTS

| | | | |
|---|---|---|---|
| 3,576,033 | 4/1971 | Tesoro et al. | 260/448.8 R |
| 3,657,303 | 4/1972 | Golitz et al. | 260/448.2 N |
| 3,658,864 | 4/1972 | Golitz et al. | 260/448.2 N |
| 3,676,478 | 7/1972 | Golitz et al. | 260/448.2 N |
| 3,725,449 | 4/1973 | Golitz et al. | 260/448.8 R |
| 3,772,351 | 11/1973 | Wrahnke | 260/448.2 N |

*Primary Examiner*—Allen B. Curtis
*Attorney, Agent, or Firm*—Gene Harsh; Joseph C. Gil

[57] ABSTRACT

The instant invention is directed to a process of preparing a silyl substituted urea derivative comprising reacting an isocyanate of the formula

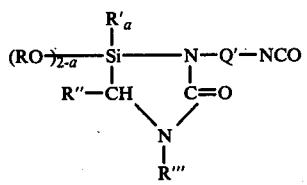

wherein
R represents a $C_1$–$C_{18}$ alkyl group, a $C_4$–$C_{14}$ cycloalkyl group or a phenyl group,
R' represents an optionally halogenated or cyano-substituted $C_1$–$C_{10}$ alkyl, $C_4$–$C_{10}$ cycloalkyl or $C_6$–$C_{10}$ aryl group,
R" represents a hydrogen atom, a methyl group or a phenyl group,
R'" represents a hydrogen atom or an optionally halogenated or cyano-substituted $C_1$–$C_{18}$ alkyl, $C_4$–$C_{14}$ cycloalkyl or $C_6$–$C_{14}$ aryl group,
Q' represents a divalent alkyl group containing 4 to 12 carbon atoms or a divalent $C_4$–$C_{14}$ cycloalkyl, $C_7$–$C_{15}$ aralkyl, $C_6$–$C_{14}$ aryl or $C_8$ alkylaryl group,
a = 0 or 1,
with a compound of the formula: $Q(XH)_c$, wherein
Q represents a c-valent radical derived by the removal of c-XH groups from compounds with a molecular weight of 4000 to 80,000 which contains urea and urethane groups and in addition thereto, contains groups selected from the group consisting of ester groups, ether groups, and carbonate groups,
c = 1 to 8 and
X represents NH or NY, where Y is a $C_1$–$C_8$ alkyl group, at a temperature of between $-20°$ to $150°$ C in the presence of a stabilizing amount of a secondary or tertiary alcohol.

The products so obtained have excellent storage stability, controlled reactivity and improved properties of cross-linked end products.

7 Claims, No Drawings

PROCESS FOR THE PREPARATION OF SILYL SUBSTITUTED UREA DERIVATIVES

This application is a continuation-in-part of U.S. application Ser. No. 303,183, filed Nov. 2, 1972, now abandoned.

Silyl substituted urea derivatives have been disclosed in U.S. Pat. No. 3,676,478. They are prepared by reacting aminoalkylsilane derivatives with polyethers which contain isocyanate groups. The products obtained from this reaction are suitable for use as bonding agents, surface active agents and starting materials for the preparation of organopolysiloxanes. An important feature of these silyl substituted urea derivatives is their synthesis for polyethers which contain only one urethane group for each hydroxyl group of the polyether, i.e. they have a very low urethane group concentration, and moreover the only urea groups they contain are silyl substituted urea end groups. These products are not suitable for the production of high quality films which can be cross-linked in the cold, light fast lacquers, fibers, coatings and sheet structures which are endowed with great toughness, strength, hardness, abrasion resistance and tear resistance and high elasticity. Although they are very reactive towards moisture they are not stable in storage and owing to their poor mechanical properties they are unsuitable for practical use. British Patent No. 1,207,594 teaches the preparation of vulcanizable polymers by reacting isocyanates terminated polyurethanes and/or polyureas with an organosilicone compound which has a reactive hydrogen atom capable of reacting with an organic isocyanate group. The compounds prepared according to this British patent are, however, no aminomethyl alkoxysilane derivatives and show for this reason a reactivity which is far below the reactivity of such aminomethyl alkoxysilane derivatives. The reactivity of aminomethyl-alkoxysilane derivatives is in fact at least 1000 times higher than the reactivity of the compounds described in this British patent. Furthermore due to the absence of aminomethyl alkoxysilane groups in the starting materials which are used according to British Patent No. 1,207,594 cyclic systems of the kind described hereinafter are not obtained according to the process of this British patent. A further difference between the teaching of British Patent No. 1,207,594 and the present invention resides in the fact that according to British Patent No. 1,207,594 organosilicone compounds containing active hydrogen atoms are reacted with isocyanate terminated prepolymers whereas according to the present invention compounds containing active hydrogen atoms are reacted with organosilicone compounds which do not contain active hydrogen atoms but isocyanate groups. Polymer compounds containing aminomethylalkoxysilane derivatives which are not only very stable in storage but also highly reactive in their application as well as giving rise to high quality end products have not previously become known.

These technically advantageous products are now made available by this invention.

It has now surprisingly been found that the high reactivity of polyaddition compounds which contain α-aminomethyl-alkoxysilane derivatives, even those which have a very high molecular weight, can be controlled to serve a variety of different technically useful purposes. Thus while retaining the excellent storage stability the reactivity can be either increased or moderated according to the desired field of application of the products. Furthermore, the properties of the cross-linked end products can be very greatly improved compared with those obtainable by the prior art. Trouble-free synthesis of the polyaddition products can be carried out in spite of the extremely high reactivity of the products towards moisture. According to a particularly advantageous embodiment of the invention, this can be achieved by the synthesis of those polyaddition products which by virtue of their hydrogen bridge bonds and molecular association have a pronounced tendency to association and by using previously unknown selectively stabilizing substances for the synthesis.

This invention relates to the preparation of silyl substituted urea derivatives of the formula I:

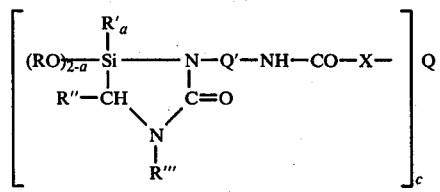

wherein
R represents a $C_1$-$C_{18}$ alkyl group, a $C_4$-$C_{14}$ cycloalkyl group or a phenyl group,
R' represents an optionally halogenated or cyano-substituted $C_1$-$C_{10}$ alkyl, $C_4$-$C_{10}$ cycloalkyl or $C_6$-$C_{10}$ aryl group,
R'' represents a hydrogen atom or a methyl group or a phenyl group,
R''' represents a hydrogen atom or an optionally halogenated or cyanosubstituted $C_1$-$C_{18}$ alkyl, $C_4$-$C_{14}$ cycloalkyl or $C_6$-$C_{14}$ aryl group,
Q' represents a divalent alkyl group containing 4 to 12 carbon atoms or a divalent $C_4$-$C_{14}$ cycloalkyl, $C_7$-$C_{15}$ aralkyl, $C_6$-$C_{14}$ aryl or $C_8$ alkylaryl group,
Q represents a c-valent radical derived by the removal of c-XH groups from compounds with a molecular weight of 4000 to 80,000 which contain urea and urethane and in addition thereto contains groups selected from the group consisting of ester groups, ether groups and carbonate groups,
a = 0 or 1,
c = 1 to 8, preferably 2 or 3,
X represents NH or NY, where Y is a $C_1$-$C_8$ alkyl group.

This invention also relates to a process for the preparation of silyl substituted urea derivatives by reacting an isocyanate of the formula II:

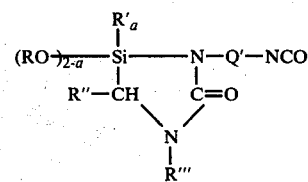

in which R, R', R'', R''', Q' and a have the meanings already indicated if desired in the form of a masked isocyanate, with a compound of the formula III:

in which Q, X and c have the meaning already indicated, the reaction being carried out at a temperature of between −20° and 150° C., in the presence of a stabilizing amount of a secondary or tertiary alcohol.

Isocyanates of the said general formula II are obtained by reacting diisocyanates of the general formula IV:

$$Q'(NCO)_2$$

in which Q' has the meaning already indicated with compounds of the general formula V:

$$(RO)_{\overline{3-a}}-Si(R')_a-\underset{R''}{\overset{|}{C}}H-\underset{R'''}{\overset{|}{N}}H$$

in which R, R', R'', R''' and a have the meanings already indicated.

Examples of diisocyanates of the general formula IV include known aliphatic, cycloaliphatic, araliphatic and aromatic diisocyanates, for example tetramethylene-1,4-diisocyanate, hexamethylene-1,6-diisocyanate, dodecane-1,12-diisocyanate, cyclohexane-1,3- and -1,4-diisocyanate and any mixtures of these isomers, 1-isocyanato-3,3,5-trimethyl-5-isocyanatomethyl-cyclohexane, phenylene-1,3- and -1,4-diisocyanate, tolylene-2,4- and -2,6-diisocyanate and any mixtures of these isomers, m-xylylene-diisocyanate, hexahydrotolylene-2,4- and -2,6-diisocyanate and any mixtures of these isomers, 4,4'-diisocyanato-dicyclohexylmethane, diphenylmethane-4,4'-diisocyanate, diphenylpropane-4,4'-diisocyanate, naphthylene-1,5-diisocyanate, diisocyanates containing carbodiimide isocyanate adducts, which may be prepared according to German Patent Specification No. 1,092,007, the diisocyanates described in U.S. Pat. No. 3,492,330, the diisocyanates prepared by telomerization reactions described in Belgian Patent Specification No. 723,640, the diisocyanates which contain ester groups described in British patent specification Nos. 956,474 and 1,072,956, the aliphatic, cycloaliphatic, araliphatic and aromatic diisocyanates mentioned by W. Siefgen in Justus Liebig's Annalen der Chemie, 562, pages 75–136, reaction products of the above-mentioned isocyanates with acetals according to German Patent Specification No. 1,072,385 and the isocyanates mentioned in German Patent Specification Nos. 1,022,789 and 1,027,394.

Any mixtures of the above-mentioned diisocyanates may, of course, be used.

It is generally preferred to use commercially readily available diisocyanates, e.g. tolylene-2,4- and -2,6-diisocyanate and any mixtures of these isomers, m-xylylene diisocyanate and 4,4'-diisocyanato-dicyclohexylmethane.

Tetramethylene-1,4-diisocyanate, hexamethylene-1,6-diisocyanate, 1-isocyanato-3,3,5-trimethyl-5-isocyanato-methylcyclohexane, m-xylylene diisocyanate, 4,4'-diisocyanato-dicyclohexyl-methane and 4,4'-diisocyanato-diphenyl methane are also preferred.

The folloiwng compounds are examples of aminoalkylsilane derivatives of the formula V in which R, R', R'', R''' and a have the meanings already indicated which are used for preparing the isocyanates from which are obtained the silyl-substituted urea derivatives according to the invention:

$$C_6H_{11}-NH-CH_2-Si(-OC_2H_5)_3$$

-continued $$C_6H_{11}-NH-CH_2-\underset{OC_2H_2}{\overset{|}{Si}}(-O-tert.\ butyl)_2$$

$$C_6H_{11}-NH-CH_2-\underset{CH_3}{\overset{|}{Si}}-(OC_2H_5)_2$$

$$C_6H_{11}-NH-CH_2-Si(OC_4H_9)_3$$

$$C_6H_5-CH_2-NH-CH_2-Si(-OC_2H_5)_3$$

$$C_6H_{11}-NH-CH_2-\underset{CH_3}{\overset{\overset{\displaystyle CH_3}{|}}{Si}}-(-O-\underset{CH_3}{\overset{|}{C}}H)_3$$

$$C_4H_9-NH-CH_2-\underset{CH_3}{\overset{|}{Si}}(OC_2H_5)_2$$

$$CH_3-\underset{CH_3}{\overset{\overset{\displaystyle CH_3}{|}}{C}}-NH-CH_2-Si(-OC_2H_5)_3$$

$$\underset{H_3C}{\overset{H_3C}{\diagdown}}N-NH-CH_2-Si(-OC_2H_5)_3$$

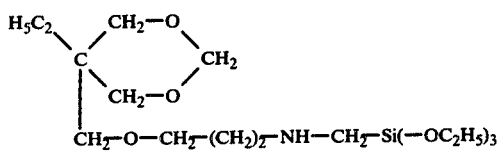

These aminoalkylsilane derivatives may be prepared by the methods described in German Offenlegungsschrift Nos. 1,812,564 and 1,812,562 (U.S. Pat. No. 3,676,478). In general, they may be prepared, for example, by reacting amines of the formula R'''—NH₂ with, for example, chloromethyl-triethoxysilane, bromomethyl-triethoxysilane, methyl-chloromethyl-diethoxysilane, dimethyl-chloromethyl-ethoxysilane, methyl-bromomethyl-diethoxysilane or methyl-bromomethyl-di-n-propoxysilane.

Examples of isocyanates of the formula

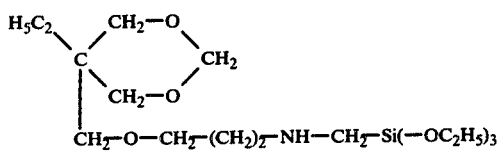

are compounds of the following formulae:

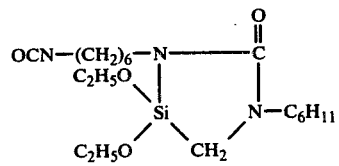

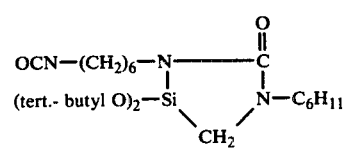

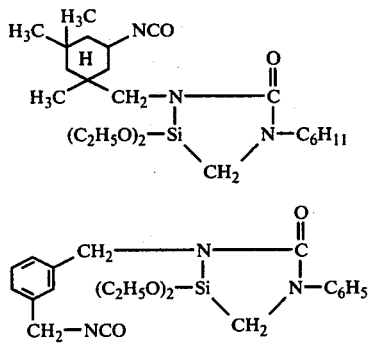

For the process of the invention, the compounds of the formula $Q(XH)_c$ can be:
(a) amino-containing polyaddition products of polyisocyanates, amino-containing chain lengthening agents and polyesters with a molecular weight of 400 to 4000 which contain at least two hydroxyl groups, which polyesters may be prepared e.g. by reacting adipic acid or phthalic acid with, for example, ethylene glycol, butylene glycol, hexane-1,6-diol or neopentyl glycol or;
(b) amino-containing polyaddition products of the said polyisocyanates, amino-containing chain-lengthening agents and polyethers which have a molecular weight of 400 to 4000, e.g. the polyethers which may be obtained by the polymerization of tetrahydrofuran; or
(c) amino-containing polyaddition products of the said polyisocyanates, chain lengthening agents and polycarbonates of a molecular weight of 400 to 4000 which contain at least two hydroxyl groups, which polycarbonates may be prepared e.g. by reacting hexane-1,6-diol with diphenyl carbonate. Polycarprolactone polyols may also be used as the hydroxyl containing component.

The following are preferred chain-lengthening agents used in the preparation of these compounds: ethylene diamine, trimethylenediamine, hexamethylene-1,6-diamine, 1-amino-3,3,5-trimethyl-5-aminomethyl-cyclohexane, 4,4'-diamino-dicyclohexylmethane, hydrazine, hydrazine hydrate, carbodihydrazide and 4,4'-diamino-diphenylmethane.

The compounds of the formula $Q(XH)_c$ will necessarily contain both urethane and urea groups and will also contain carbonate groups, ester groups or ether groups depending upon which hydroxyl containing reactant is chosen. The compounds of the formula $Q(XH)_c$ are normally prepared by reacting the polyhydroxyl compounds which have a molecular weight of 400 to 4000 with an excess of the polyisocyanate and subsequently reacting the NCO-prepolymers thus obtained with the amino-containing chain-lengthening agent.

The reaction of the above-mentioned components to produce the products according to the invention is generally carried out in the presence of an inert solvent, e.g. benzene, toluene, cyclohexane, acetone, ethyl acetate, tetralin or dimethylformamide. It has surprisingly been observed that the products of the invention can be obtained in a stable form in which they can be stored if the reaction according to the invention is carried out in the presence of a stabilizing amount of secondary or tertiary alcohols. According to a process of the instant invention, therefore, the solvent consists completely or partly of secondary or tertiary alcohols. The secondary or tertiary alcohols are used in reaction stabilizing amounts and are preferably present in amounts of from 10 to 80% by weight based on the total amount of reactants. Premature gelling, cross-linking or sedimentation of the reaction products dissolved in the solvent is thereby prevented.

Suitable secondary and tertiary alcohols are isopropanol, isobutanol, cyclohexanol, tertiary amyl alcohol, tertiary butanol, and benzyl alcohol. Isopropyl alcohol and tertiary butanol are preferred. Preferred solvent mixtures are toluene/isopropanol (1:1), toluene/tertiary butanol (1:1) xylene/isopropanol/ethanol (1:1:1), and toluene/tertiary butanol/n-butanol (1:1:1).

The stabilizing effect of the secondary or tertiary alcohols may be enhanced and at the same time the reactivity of the products of the process towards atmospheric moisture in the cross-linking reaction may be greatly increased by adding small quantities of acid anhydrides and acids or compounds which split off acids. The activating effect of these acid additives comes into play during the evaporation process while if they are present in solutions kept in closed containers they will keep the viscosity of the solutions completely constant within the limit of error of measurement over a period of 6 months. This combined stabilizing and activating effect obtained when carrying out the cross-linking reactions is of great practical importance because it not only effects prolonged stabilization of solutions kept in vessels which are sealed against atmospheric moisture but also enables very rapid cross-linking reactions to be carried out whenever required, even at temperatures of about $-10°$ C. The new compounds according to the invention, which are highly reactive and very readily cross-linked via the siloxane groups can therefore be converted into products which are stable in storage. Hence a very wide field of application is opened up to these new polymers which can easily be cross-linked whenever required. The polymers synthesized by this method take up a previously unattained position of supremacy in the chemistry of cross-linkable high molecular weight polymers by virtue of their high rate of cross-linking and the quantitative course of the cross-linking reaction to form stable polysiloxane bonds.

The process according to the invention enables the synthesis of a wide variety of polymers and which can be cross-linked in the cold by atmospheric moisture or by aqueous organic solvents or moist inert gases and which, if desired, can be cross-linked even at temperatures below $0°$ C. without catalysts, without additional cross-linking agents and without heat.

The following are given as examples of acids, acid anhydrides or compounds which split off acids which in accordance with this invention have an additional stabilizing effect and an activating effect when the products according to the invention are cross-linked by atmospheric moisture: acetic anhydride, acetic acid, formic acid, propionic acid, butyric acid, trichloroacetic acid, p-toluene sulphonic acid esters, dimethylcarbamic acid chloride, benzoyl chloride, N-phenylcarbamic acid chloride, chloroacetaldehyde, chloral, propionic anhydride, mixed anhydrides of lower carboxylic acids, cyclic anhydrides such as maleic anhydride, phthalic anhydride and tetrahydrophthalic anhydride, semiesters of cyclic anhydrides, e.g. semiesters of 1 mol of phthalic anhydride and 1 mol of methanol, butanol or isopropanol or semiesters of these cyclic acid anhydrides with glycols which contain both an OH group and a carboxyl group, e.g. semiesters of 1 mol of maleic anhydride or hexahydrophthalic anhydride and 1 mol of glycol, 1,3-propylene glycol or 1,4-butanediol. The addition of small quantities of readily hydrolyzed esters such as boric acid ester, diethyloxalate or ethylorthoformate or of reaction products of p-toluenesulphonylisocyanate and alcohols or amines or the addition of small quantities of p-toluenesulphonylisocyanate or of acylisocyanates such as benzoylisocyanate or of hydrochlorides of trimethylamine, triethylamine and the like may also be advantageous. These compounds which both function as stabilizers and accelerate the cross-linking process are advantageously added in quantities of 0.2 to 5% by weight, based on total solids to solutions of the products of the process in alcohol mixtures.

Known active or inactive fillers may be added to the products of the invention, e.g. chalk, talcum, silica, silica gel, quartz powder, titanium dioxide, iron oxides, zirconium silicate, calcium sulphate, aluminum oxide, magnesium oxide, carbon black, graphite, sand or known finely dispersed fillers based on silicon dioxide. All these fillers are either added in a highly dehydrated form or rendered anhydrous by dehydration in the particular stabilizing alcohols mentioned above and their acid additives.

The products according to the invention, and especially the products which have been stabilized according to the invention, are high quality products which are cold hardened by moisture or masked compounds which split off water, i.e. they are cross-linked extremely easily without supply of heat. They can be converted into a large variety of end products, e.g. elastic or hard cross-linked polymers with high chemical resistance and temperature resistance. They may be used for the production of highly elastic films, very light fast and chemically resistant lacquers and coatings on supports of any kind, rubbery elastic articles, fibers or sealing compounds of any kind. They may also be used for embedding electrical appliances, for insulation against cold or heat, for laminating various pigments, for providing elastic coverings for various water-soluble plant nutrient salts and as medicaments; they may also be used as anticorrosive compounds, as adhesives for metals such as silver, aluminum or copper, as adhesive, non-cross-linking water repellents, as rapidly cross-linking surface active compounds, as laminating and rubberizing agents for fibers and fleeces and for bonding fleeces; they are also excellent adhesives. According to the invention, many different synthetic resin segments can be cross-linked via siloxane bridges and combined with each other, and in many cases aminoalkylsilane derivatives of the following general formula which has already been mentioned above:

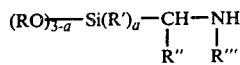

in which R, R', R", R'" and a have the meanings already indicated above are added to the products of the invention in quantities of 2 to 60% by weight during the cross-linking reaction as a means of controlling the adhesive power, degree of cross-linking and tendency to swell. The use of products which are stabilized and then activated when put into use in accordance with the invention opens up the possibility of new economic techniques for coating, impregnating and tack-free sheathing of any synthetic or natural fibers or threads. These materials can now be coated without sticking and quickly rolled up without sticking. Rapid insulation of cables by dip varnishing and dip coating, the production of cable sheathings for wire lacquering which rapidly complete their chemical and physical reactions and the use of rapidly cross-linking substances which have good adhesive and bonding properties can now be carried out easily and simply. The possibility of rapid and non-sticky covering of pigments which contain moisture is also of considerable interest.

The products according to the invention may, if desired, be mixed with organopolysiloxanes which can be cross-linked in known manner, e.g. those organopolysiloxanes which are prepared by the condensation of chlorosilanes and alkoxysilanes by cohydrolysis with water or by the polymerization of cyclic organosiloxanes by means of alkaline or acid catalysts and which are then cross-linked, e.g. together with $\alpha,\omega$-dihydroxypolydimethylsiloxanes. The products of the process are also very interesting reactive compounds for carrying out matrix reactions in accordance with Belgian Patent Specification No. 746,982 and for impregnating foam resins.

The new compounds according to the invention also enable the production of synthetic resins which can be cross-linked in the cold by moisture, e.g. the production of elastic, very light-fast coatings and lacquers which can be firmly bonded to various metals and noble metals simply by quickly dipping the metal articles, e.g. metal sheets or shaped metal parts, into these substances. They may also be used for the production of elastic and abrasion resistant semi-hard or hard synthetic resin lacquers.

Another important use of the substances according to the invention is the high quality finishing of paper, textiles and foam resins, particularly polyurethane foams. The controlled cross-linking which can be achieved in these products which are stabilized according to the invention and contain alcohols and acid additives enables particularly elegant methods of application to be employed. It is particularly advantageous that the activating effect of these acid additives does not come into play until the products are applied, namely, during the evaporation of the solvent mixtures which contain alcohols, while in closed containers these acid additives ensure complete constancy of the viscosity of the products. Controlled cross-linking of the products according to the invention, however, sets in immediately as soon as the alcohol concentration drops, for example, when a film starts to dry in the presence of atmospheric moisture. This controlled cross-linking of the products, i.e., controlled in the sense that it can be made to take place whenever required, e.g. in the presence of atmospheric moisture, can be accelerated to such an extent by the acid additives that it can be completed in the cold in only a few minutes; this cross-linking results in the formation of polysiloxane bridge members.

The invention is further illustrated but is not intended to be limited by the following examples in which all parts and percentages are by weight unless otherwise specified.

EXAMPLE 1

An anhydrous mixture of 110 parts by weight of a polyester of adipic acid and 1,4-butylene glycol (OH number 52) and 81 parts by weight of a polyester of adipic acid, hexanediol and neopentylglycol (molar ratio 30:22:12, OH number 66), reacted with 44.4 parts by weight of 1-isocyanato-3,3,5-trimethyl-5-isocyanatomethylcyclohexane to produce the α,ω-NCO prepolymer. The NCO prepolymer is diluted with 100 parts by volume of toluene and added dropwise at 25° C. in the course of 20 minutes, with vigorous stirring, to a solution of 22 parts by weight of 1-amino-3,3,5-trimethyl-5-aminomethylcyclohexane in 1102 parts by weight of an anhydrous solvent mixture of toluene and tertiary butanol (1:1). Average molecular weight of the resulting α,ω-diaminopolyurea: 8700. 29 parts by weight of the following isocyanato-5-silaimidazolidone-(2) derivative mixture (A + B) dissolved in 28 parts by weight of toluene are then introduced dropwise with stirring:

Composition of the mixture:

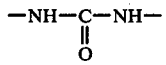

(A) 78% by weight

OCN—(CH₂)₆—N(Si(OC₂H₅)₂)—CH₂—C(=O)—N—C₆H₁₁ and (B) 21.2% by weight

C₂H₅—O—C(=O)—NH—(CH₂)₆—N(Si(OC₂H₅)₂)—CH₂—C(=O)—N—C₆H₁₁

NCO content of the mixtures (A + B) = 8.8%.

This mixture was obtained by reacting 1 mol of N-cyclohexyl-(aminomethyl)-triethoxysilane with an excess of 6 mols of hexamethylene diisocyanate at room temperature and immediately distilling off excess hexaymethylene diisocyanate in a thin layer evaporator at 140° C. Ethanol is split off and the 1:1 adduct under goes ring closure with formation of imidazolidone, most of the alcohol distilling off and only a small part remaining bound as ethylurethane in product B.

The reaction of the α,ω-diamino-polyurethane polyureas with the above-mentioned mixtuure (A + B) results in a solution of polyurethane polyureas with 5-silaimidazolidone-(2) end groups which is stable in storage and very reactive with moisture. The monomer B acts as a chain lengthening or cross-linking agent in the cross-linking process and is incorporated quantitatively. The polyaddition product can be cross-linked in a cellular form with residual moisture in polyurethane foams by matrix reactions to produce light fast foams. Very light fast, completely non-tacky, cross-linked, open-celled foams which have a density of 75 kg/m³ and a much higher tear resistance than the matrix used are obtained.

EXAMPLE 2

This example demonstrates that polyurethane polyureas which contain reactive alkoxysilane end groups and high concentrations of

—NH—C(=O)—NH— groups and which are stable in storage and do not undergo premature cross-linking and the solutions of which are free from gel particles can be obtained by the process according to the invention.

220 parts by weight (0.1 mol) of an anhydrous polyester of adipic acid and butane-1,4-diol (OH number 51) are reacted with 44.4 parts by weight of 1-isocyanato-3,3,5-trimethyl-5-isocyanatomethylcyclohexane (0.2 mol) to produce the α,ω-diisocyanatoprepolymer which is then diluted with a solution of 44.4 parts by weight of 1-isocyanato-3,3,5-trimethyl-5-isocyanatomethyl-cyclohexane (isophorone diisocyanate) (0.2 mol) in 100 parts by weight of toluene at 95° C. The solution obtained contains 0.1 mol of a macrodiisocyanate (NCO prepolymer) and 0.2 mol of the monomeric isophorone diisocyanate. This solution is cooled to 45° C. and added dropwise in the course of 20 minutes to a solution of 58 parts by weight of 1-amino-3,3,5-trimethyl-5-amino-methyl-cyclohexane (= isophorone diamine) in 620 parts by weight of toluene and 720 parts by weight of tertiary butanol at 22° C. with vigorous stirring. A water clear solution of a polyurethane polyurea which contains α,ω-diamino end groups and has a viscosity of 48 centipoises is obtained. Average molecular weight of the α,ω-diamino-polyurethane-polyureas: approximately 7600, NH₂/NCO equivalent ratio = 1.14.

43.6 parts by weight of the isocyanato-5-silaimidazolidone-(2) mixture described in Example 1 (NCO content 8.8%) in the form of a 50% solution in toluene are added to the above solution with vigorous stirring. A solution which is stable in storage and has a viscosity of 250 centipoises at 21° C. is obtained. The films obtained by casting the solution on supports such as wood, sheet metals, woven fabrics, leather and synthetic resins such as polyvinyl chloride, polyurethanes or polyesters are firmly adhering, elastic, cross-linked, hard lacquer coatings which have maximum light fastness and good chemical resistance.

The polyaddition product can be cross-linked in a cellular form in open celled, elastic polyurethane foams by matrix reactions with residual moisture, the amount of poly-addition product which can be cross-linked being 320% by weight, based on the quantity of matrix. A completely dust-free, cellular arrangement of material is obtained and there is an irreversibly fixed increase in volume of the combination foam of 35 volumes percent.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as is set forth in the claims.

What is claimed is:

1. A process for the preparation of a silyl substituted urea derivative solution comprising reacting (A) an isocyanate of the formula

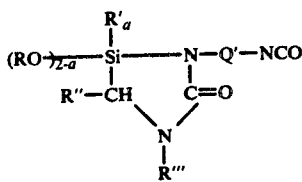

wherein
R represents a $C_1$–$C_{18}$ alkyl group, a $C_4$–$C_{14}$ cycloalkyl group or a phenyl group,
R' represents an optionally halogenated or cyano-substituted $C_1$–$C_{10}$ alkyl, $C_4$–$C_{10}$ cycloalkyl or $C_6$–$C_{10}$ aryl group,
R" represents a hydrogen atom, a methyl group or a phenyl group,
R'" represents a hydrogen atom or an optionally halogenated or cyano-substituted $C_1$–$C_{18}$ alkyl, $C_4$–$C_{14}$ cycloalkyl or $C_6$–$C_{14}$ aryl group,
Q' represents a divalent alkyl group containing 4 to 12 carbon atoms or a divalent $C_4$–$C_{14}$ cycloalkyl, $C_7$–$C_{15}$ aralkyl, $C_6$–$C_{14}$ aryl or $C_8$ alkylaryl group,
$a = 0$ or 1,
with a compound of the formula:

$$Q(XH)_c$$

wherein

Q represents a c-valent radical derived by the removal of c-XH groups from compounds with a molecular weight of 4000 to 80,000 which contains urea and urethane groups and in addition thereto, contains groups selected from the group consisting of ester groups, ether groups, and carbonate groups,
$c = 1$ to 8 and
X represents NH or NY, where Y is a $C_1$–$C_8$ alkyl group, at a temperature of between $-20°$ to $150°$ C. in the presence of a stabilizing amount of a secondary or tertiary alcohol.

2. The process of claim 1 wherein said secondary or tertiary alcohol is used in an amount of from 10 to 80 percent by weight, based on the total weight of reactants.

3. The process of claim 2 wherein R' represents a halogenated or cyano-substituted $C_1$–$C_{10}$ alkyl, $C_4$–$C_{10}$ cycloalkyl or $C_6$–$C_{10}$ aryl group.

4. The process of claim 2 wherein R'" represents a halogenated or cyano-substituted $C_1$–$C_{18}$ alkyl, $C_4$–$C_{14}$ cycloalkyl or $C_6$–$C_{14}$ aryl group.

5. The process of claim 2 wherein $c = 2$ or 3.

6. The process of claim 2 wherein said alcohol is selected from the group consisting of isopropanol, isobutanol, cyclohexanol, tertiary amyl alcohol and tertiary butanol.

7. The solution produced according to the process of claim 2.

* * * * *